(12) United States Patent
Nakamura et al.

(10) Patent No.: US 8,859,818 B2
(45) Date of Patent: Oct. 14, 2014

(54) ELECTROPHOTOGRAPHIC PHOTORECEPTOR

(75) Inventors: Junji Nakamura, Hiratsuka (JP); Tohru Kobayashi, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 13/184,814

(22) Filed: Jul. 18, 2011

(65) Prior Publication Data

US 2012/0022293 A1    Jan. 26, 2012

(30) Foreign Application Priority Data

Jul. 21, 2010    (JP) ................. 2010-164044

(51) Int. Cl.
| | |
|---|---|
| C07C 211/00 | (2006.01) |
| G03G 5/147 | (2006.01) |
| C07C 217/80 | (2006.01) |
| G03G 5/06 | (2006.01) |
| G03G 5/05 | (2006.01) |
| C07C 211/54 | (2006.01) |
| G03G 5/047 | (2006.01) |

(52) U.S. Cl.
CPC .......... *G03G 5/0614* (2013.01); *G03G 5/14708* (2013.01); *C07C 217/80* (2013.01); *G03G5/14756* (2013.01); *G03G 5/0672* (2013.01); *G03G 5/0564* (2013.01); *G03G 5/0668* (2013.01); *C07C 211/54* (2013.01); *G03G 5/047* (2013.01)
USPC ........................................................ 564/433

(58) Field of Classification Search
CPC ...................................................... G03G 5/0614
See application file for complete search history.

(56) References Cited

U.S. PATENT DOCUMENTS

| | | | |
|---|---|---|---|
| 4,769,302 | A | 9/1988 | Ueda |
| 5,736,284 | A | 4/1998 | Kobayashi et al. |
| 5,942,615 | A | 8/1999 | Kobayashi et al. |
| 6,083,651 | A | 7/2000 | Kobayashi et al. |
| 2008/0248330 | A1 | 10/2008 | Joo et al. |
| 2008/0272693 | A1 | 11/2008 | Heil et al. |

FOREIGN PATENT DOCUMENTS

| | | |
|---|---|---|
| DE | 37 15 853 A1 | 11/1987 |
| DE | 10 2005 058543 A1 | 6/2007 |
| JP | 64-013553 A | 1/1989 |
| JP | 7-168382 A | 7/1995 |
| JP | 09-295969 A | 11/1997 |
| JP | 10-059952 A | 3/1998 |
| JP | 10-255979 A | 9/1998 |
| JP | 2008-076809 A | 4/2008 |

OTHER PUBLICATIONS

Trippett, S. Pure and Applied Chemistry, 1964, vol. 9, No. 2, pp. 255-269).*
Japanese Patent Office, Japanese Office Action issued in corresponding JP Application No. 2010-164044, dated Aug. 23, 2012.
European Patent Office, European Search Report issued in corresponding EP Application No. 11174906.5, dated Aug. 2, 2012.

* cited by examiner

*Primary Examiner* — Clinton Brooks
(74) *Attorney, Agent, or Firm* — Sughrue Mion, PLLC

(57) ABSTRACT

An object of the present invention is to provide a charge transport material and an electrophotographic photoreceptor using the charge transport material, the charge transport material sufficiently satisfying characteristics conventionally desired for a charge transport material for an electrophotographic photoreceptor, specifically, the charge transport material having a good solubility in a binder polymer, allowing formation of a stable and high-concentration organic thin film therefrom, and having a high carrier mobility. To achieve the object, the present invention provides a tris(4-styrylphenyl)amine derivative represented by the following general formula (1):

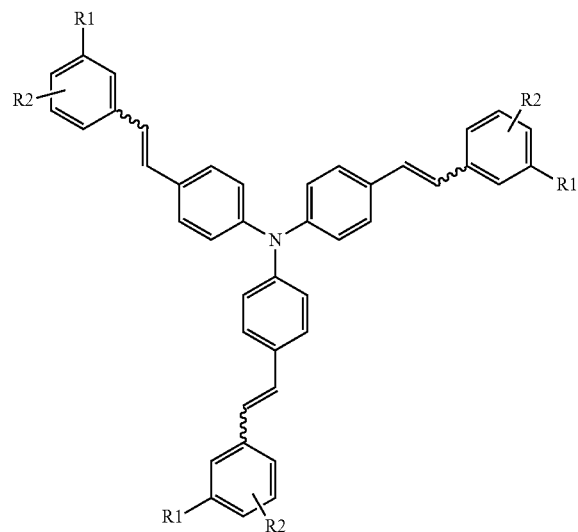
(1)
wherein R1 represents a methyl group or methoxy group, and R2 represents a hydrogen atom, methyl group, or methoxy group, provided that a case where R1 and R2 are a methyl group and R2 is at the meta-position is excluded; wherein 50% or more of geometrical isomers have three double bonds which are all trans.
1 Claim, 1 Drawing Sheet

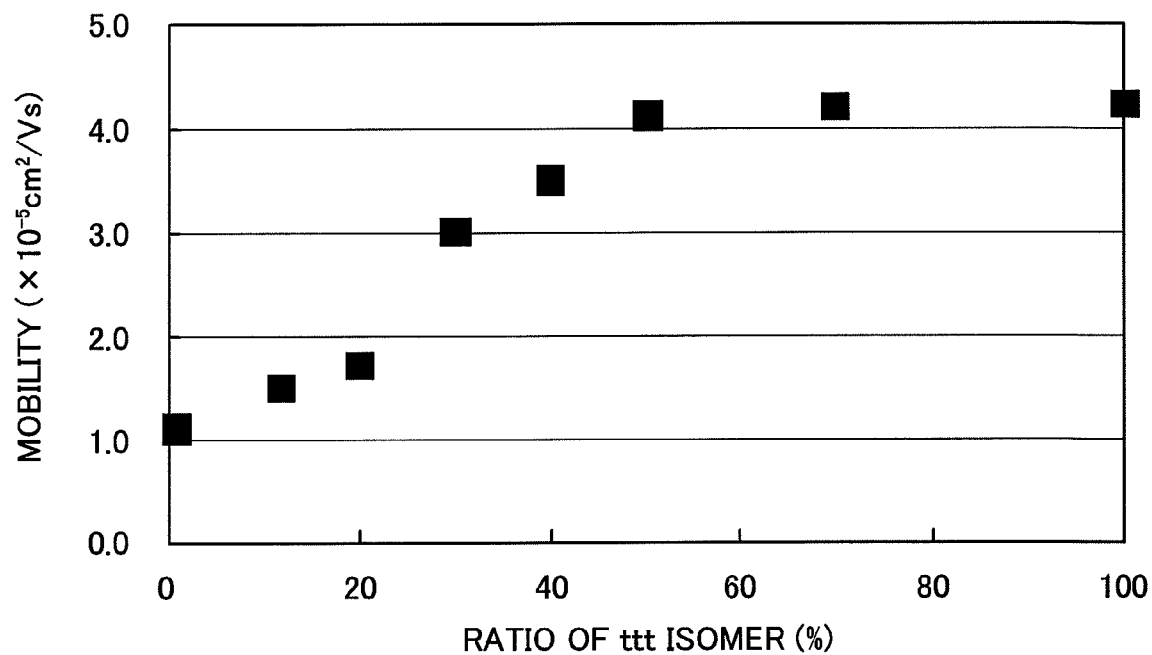

ELECTROPHOTOGRAPHIC PHOTORECEPTOR

BACKGROUND OF THE INVENTION

1. Field of the Invention

The present invention relates to an electrophotographic photoreceptor suitably usable for image forming apparatuses such as laser printers and LED printers.

2. Brief Description of the Related Art

Recently, electrophotographic photoreceptors using organic photoconductive compounds have been actively researched and studied because of, for example, their lighter weight, smoother surface, lower toxicity, greater ease of production, and lower costs than those of electrophotographic photoreceptors using inorganic photoconductive compounds. As the electrophotographic photoreceptors using organic photoconductive compounds, so-called layered photoreceptors have attracted particular attentions, and various materials have been proposed therefor. In the layered photoreceptors, the functions of the photoreceptor are achieved separately by a charge generation material and a charge transport material. In this mode, a highly sensitive electrophotographic photoreceptor may possibly be obtained by using in combination a material having a high carrier generation efficiency (carrier represents charge, hereinafter the same) as the charge generation material, and a material having a high charge transport capability as the charge transport material.

As the charge generation substances, various azo compounds and phthalocyanine-based compounds have been developed and put into practical use. Meanwhile, examples of the charge transport materials include carbazole derivatives (Japanese Patent Application Publication No. Hei 9-295969), phenothiazine derivatives (Japanese Patent Application Publication No. Hei 10-59952), tris(styrylphenyl)amine-based compounds (Japanese Patent Application Publication No. Sho 64-13553), and the like. However, the tris(styrylphenyl)amine-based compounds cannot be said to have sufficient solubilities in polymer binders and organic solvents. Moreover, even if films can be formed from the tris(styrylphenyl)amine-based compounds which are somehow made soluble, electrophotographic photoreceptors using these films do not have sufficiently high carrier mobilities. Accordingly, it cannot be said that electrophotographic photoreceptors with high sensitivity, low residual potential, and stable film state have been obtained.

SUMMARY OF THE INVENTION

An object of the present invention is to provide a charge transport material and an electrophotographic photoreceptor using the charge transport material, the charge transport material sufficiently satisfying characteristics conventionally desired for a charge transport material for an electrophotographic photoreceptor, specifically, the charge transport material having a good solubility in a binder polymer, allowing formation of a stable and high-concentration organic thin film therefrom, and having a high carrier mobility.

In order to obtain a charge transport material which can provide a stable organic thin film even when used at a high concentration, has a high carrier mobility, and allows formation of a high performance photoreceptor when used in an electrophotographic photoreceptor, the present inventors have conducted earnest studies through synthesis of various compounds. As a result, the present inventors have found that, among tris(4-styrylphenyl)amine derivatives whose substituents, substitution positions, trans/cis ratios of the double bonds, and the like may be combined in an infinite number of ways, a tris(4-styrylphenyl)amine derivative represented by the following general formula (1):

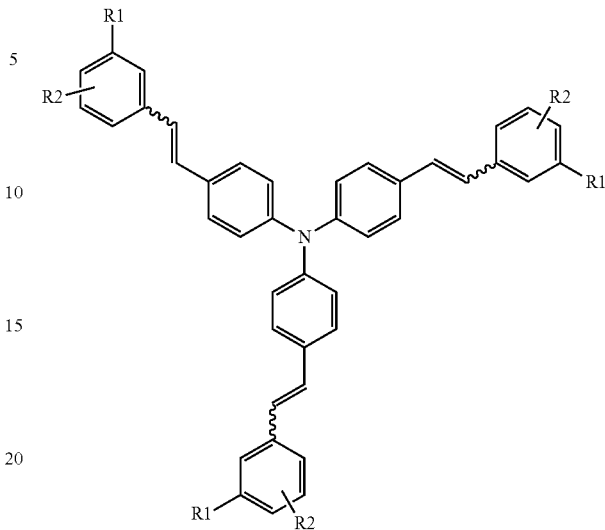

(1)

(where R1 represents a methyl group or methoxy group, and R2 represents a hydrogen atom, methyl group, or methoxy group, provided that a case where R1 and R2 are a methyl group and R2 is at the meta-position is excluded), wherein 50% or more of geometrical isomers have three double bonds which are all trans, is a charge transport material which has a good solubility in a binder polymer, allows the formation of a stable and high-concentration organic thin film, and has a high carrier mobility. This finding has led to the completion of the present invention. Specifically, it has been found that when the substituents are present in the R1 positions, the solubility is increased. Note that, the ratio of the geometrical isomer in the present invention is a value calculated on the basis of HPLC.

In other words, the present invention provides a tris(4-styrylphenyl)amine derivative represented by the following general formula (1):

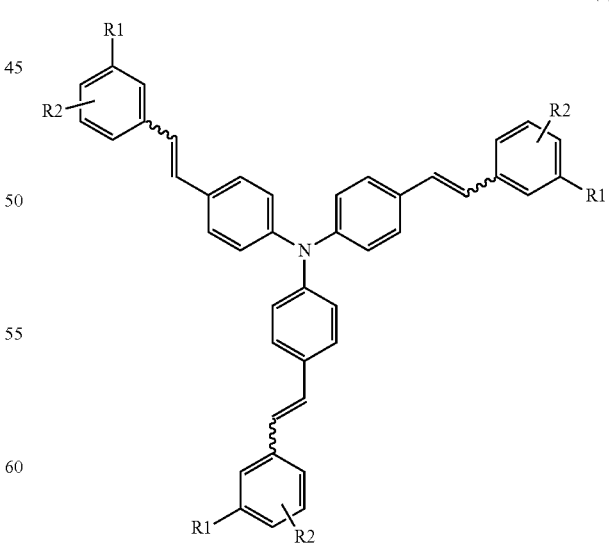

(1)

(where R1 represents a methyl group or methoxy group, and R2 represents a hydrogen atom, methyl group, or methoxy group, provided that a case where R1 and R2 are a methyl group and R2 is at the meta-position is excluded), wherein 50% or more of geometrical isomers have three double bonds which are all trans.

Moreover, the present invention provides a charge transport agent comprising the tris(4-styrylphenyl)amine derivative.

Furthermore, the present invention provides an electrophotographic photoreceptor comprising the charge transport agent.

In addition, the present invention provides a tris(4-styrylphenyl)amine derivative represented by the following general formula (1):

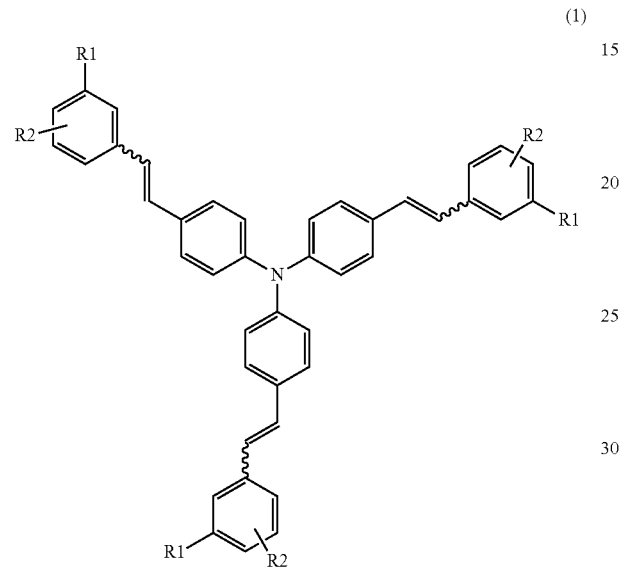

(1)

(where R1 represents a methyl group or methoxy group, and R2 represents a hydrogen atom, methyl group, or methoxy group), wherein three double bonds of the tris(4-styrylphenyl)amine derivative are all trans.

Additionally, the present invention provides a tris(4-styrylphenyl)amine derivative represented by the following general formula (2):

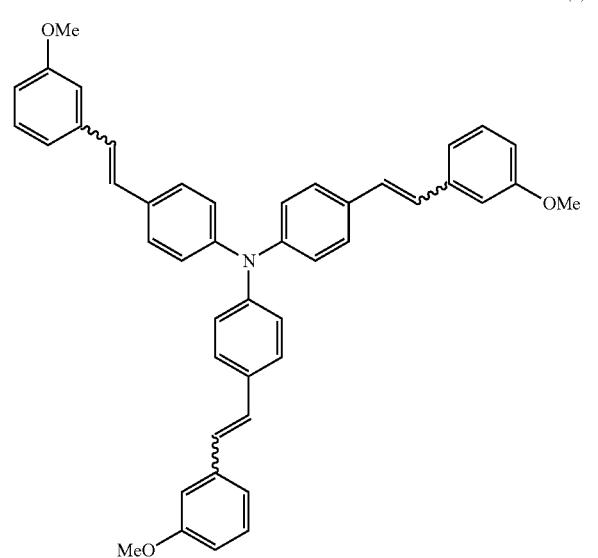

(2)

The charge transport material of the present invention is industrially excellent, because of the following reason. Specifically, the charge transport material has a high mobility. In addition, when a photoreceptor layer is formed therefrom, the film is stable, moreover has good mechanical properties, and can achieve a high sensitivity and a low residual potential.

BRIEF DESCRIPTION OF THE DRAWINGS

FIG. 1 is a graph showing the relationship between the ratio of the ttt isomer and the mobility of Compound (1-1).

DESCRIPTION OF THE PREFERRED EMBODIMENTS

Hereinafter, the present invention will be described in further details.

In a tris(4-styrylphenyl)amine derivative represented by the general formula (1) of the present invention, 50% or more of geometrical isomers have three double bonds which are all trans.

In the general formula (1), examples of R1 include methyl groups and methoxy groups, and examples of R2 include hydrogen atoms, methyl groups, and methoxy groups. The following compounds are exemplified as preferred examples of the compound represented by the general formula (1), but the present invention is not limited thereto.

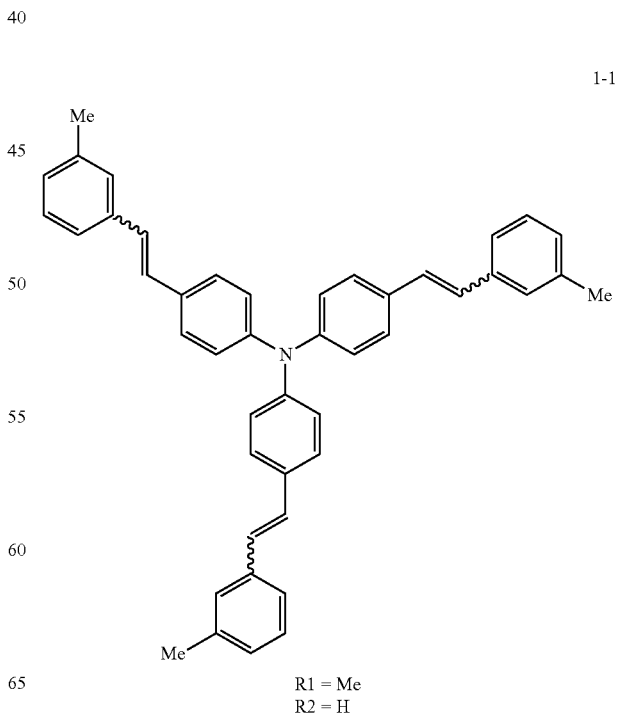

1-1

R1 = Me
R2 = H

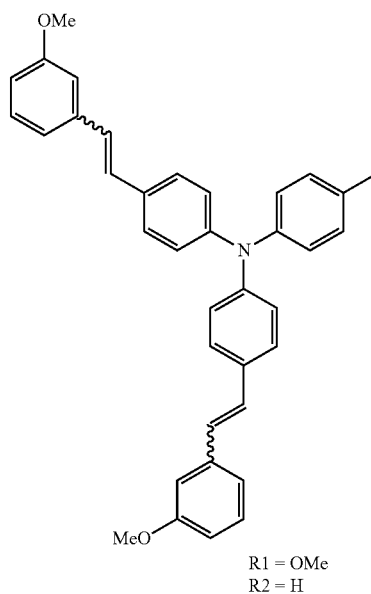

1-2

R1 = OMe
R2 = H

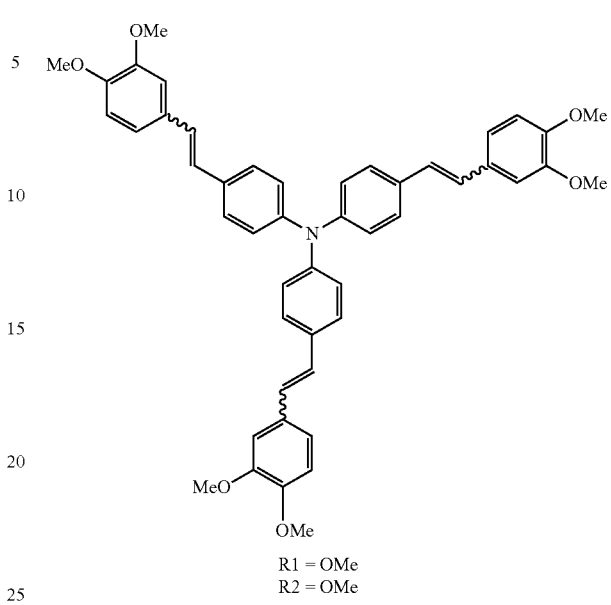

1-4

R1 = OMe
R2 = OMe 1-5

R1 = OMe
R2 = OMe

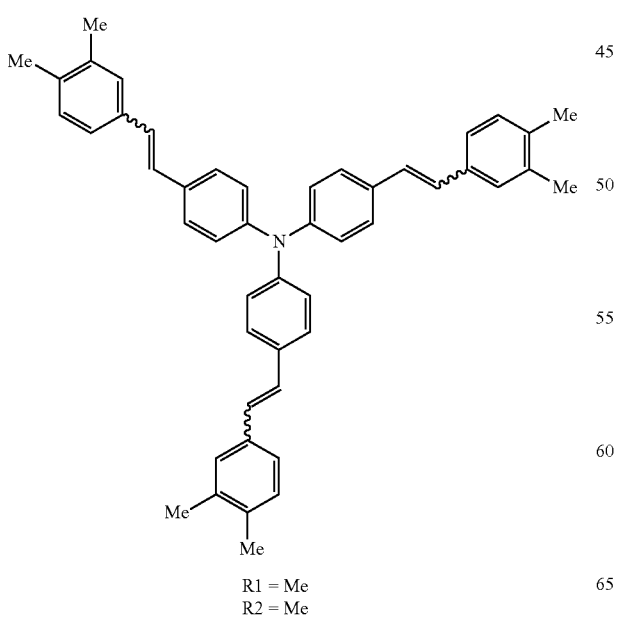

1-3

R1 = Me
R2 = Me

The tris(4-styrylphenyl)amine derivative represented by the general formula (1) has three double bonds, each of which may be in the trans or cis configuration. Hence, the following four geometrical isomers exist: a trans/trans/trans isomer, a trans/trans/cis isomer, a trans/cis/cis isomer, and a cis/cis/cis isomer (which are referred to as a ttt isomer, a ttc isomer, a tcc isomer, and a ccc isomer, respectively). These four types of isomers can be separated from one another by HPLC. Here, a tris(4-styrylphenyl)amine derivative in which 50% or more of geometrical isomers have three double bonds which are all trans in the present invention means that the ratio of the ttt isomer among the four geometrical isomers is 50% or higher based on HPLC analysis. As a result of our diligent examination, it has been found that a higher mobility can be achieved than that of 4-(2,2-bisphenyl-ethene-1-yl)-4',4''-dimethyl-triphenylamine, which is generally used as a high mobility charge transport material in the cases where the ratio of the ttt isomer of the general formula (1) is 50% or higher, among cases with various ratios.

The above-described tris(4-styrylphenyl)amine derivative represented by the general formula (1) is synthesized, for example, as follows. Note that, in the following formula, each R1 and each R2 have the same meanings as described above.

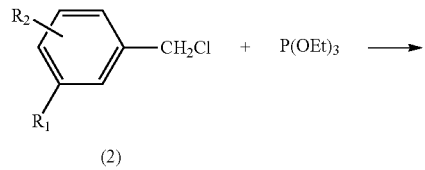
(2)

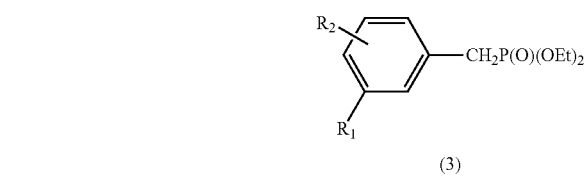
(3)

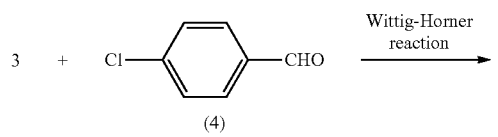
(4)

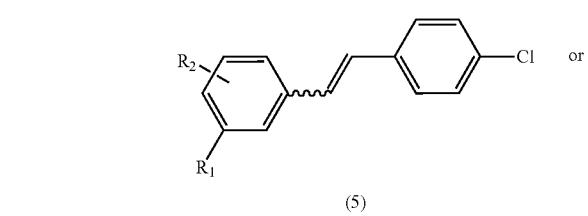
(5)

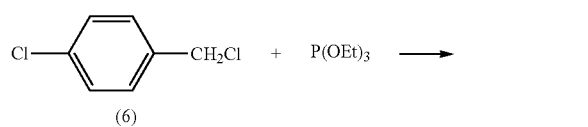
(6)

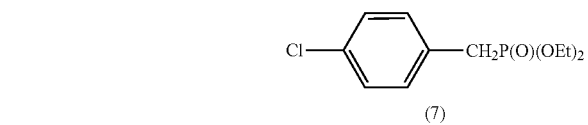
(7)

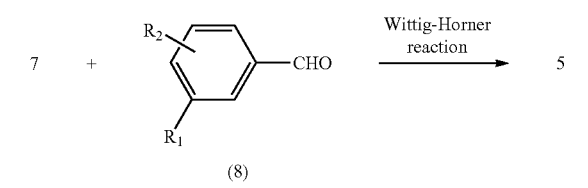
(8)

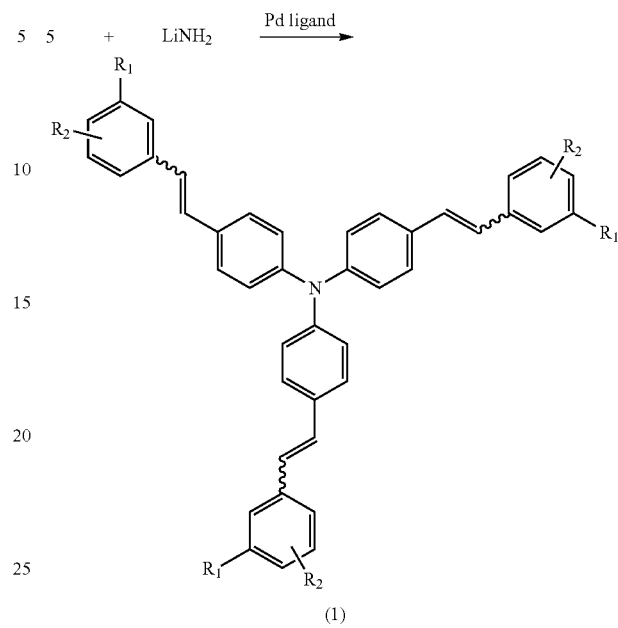
(1)

First, a benzyl chloride derivative (2) is allowed to react with triethyl phosphite to prepare a Wittig-Horner reagent (3), which is then allowed to react with p-chlorobenzaldehyde to obtain a stilbene derivative (5). Alternatively, the stilbene derivative (5) can be obtained in such a manner that p-Chlorobenzyl chloride (6) is allowed to react with triethyl phosphite to prepare a Wittig-Horner reagent (7), which is then allowed to react with a benzaldehyde derivative (8). The thus obtained stilbene derivative (5) is a mixture of the cis isomer and the trans isomer. However, a mixture enriched with the trans isomer can be obtained through column chromatography, recrystallization, distillation, or the like. Subsequently, in accordance with the method of Buchwald et al (Org. Lett. 2001, 3, 3417.), the stilbene derivative (5) enriched with the trans isomer is allowed to react with lithium amide in the presence of a metal such as Pd and a phosphorus atom-containing ligand. Thus, the tris(4-styrylphenyl)amine derivative (1) can be synthesized. Examples of palladium complexes usable here include $PdCl_2$, $Pd(OAc)_2$, $[PdCl(allyl)]_2$, $Pd_2(dba)_3$, and the like. Examples of the phosphorus atom-containing ligand include triarylphosphine-based ligands such as triphenylphosphine and tri-o-tolylphosphine; trialkylphosphine-based ligands such as tri-t-butylphosphine and tricyclohexylphosphine; 2-phosphinobiphenyl-based ligands such as 2-(dicyclohexylphosphino)biphenyl, 2-(di-t-butylphosphino)biphenyl, 2-(dicyclohexylphosphino)-2',4',6'-tri-isopropyl-1,1'-biphenyl, and 2-(di-t-butylphosphino)-2'-(N,N-dimethylamino)biphenyl; olefin substituted phosphine-based ligands such as 1,1-diphenyl-2-(dicyclohexylphosphino)propene and 1,1-diphenyl-2-(di-t-butylphosphino)propene; cyclopropane ring-substituted phosphine-based ligands such as (di-t-butyl)(1-methyl-2,2,-diphenylcyclopropyl)phosphine and (dicyclohexyl)(1-methyl-2,2,-diphenylcyclopropyl)phosphine; and the like.

A charge transport agent of the present invention comprises the above-described tris(4-styrylphenyl)amine derivative. The charge transport agent of the present invention can be used, for example, for an electrophotographic photoreceptor.

An electrophotographic photoreceptor of the present invention using a charge transport agent may be a so-called multilayer type electrophotographic photoreceptor in which the functions of a photoreceptor layer are achieved separately by a charge generation layer and a charge transport layer provided on a conductive substrate, or a so-called single layer type electrophotographic photoreceptor in which a single photoreceptor layer containing a charge generation agent and a charge transport agent is provided on a conductive substrate. For the multilayer type electrophotographic photoreceptor, the charge transport layer using the tris(4-styrylphenyl)amine derivative as the charge transport agent can be formed as follows. Specifically, Compound (1) is directly vapor deposited on a conductive substrate or on a charge generation layer, or a solution obtained by dissolving the tris(4-styrylphenyl) amine derivative and a binder polymer into an appropriate solvent is applied onto a conductive substrate or a charge generation layer, and then dried. Meanwhile, for the single layer type electrophotographic photoreceptor, the photoreceptor layer is formed as follows. Specifically, a liquid obtained by dissolving or dispersing a charge generation agent, the tris(4-styrylphenyl)amine derivative, and the like, as well as a binder polymer, into an appropriate solvent is applied onto a conductive substrate, and then dried. Note that the single layer type photoreceptor may contain an electron transport material, if needed.

Examples of the binder polymer include polyacrylates, polymethacrylates, polyamides, acrylic resins, acrylonitrile resins, methacrylic resins, vinyl chloride resins, vinyl acetate resins, phenol resins, epoxy resins, polyesters, alkyd resins, polycarbonates, polyurethanes, polystyrenes, and copolymers thereof. Besides such insulating polymers, organic photoconductive polymers such as polyvinylcarbazoles, polyvinylanthracenes, and polyvinylenes can be used. Of these binder polymers, polycarbonates are particularly preferable. Examples of polycarbonates which can be used preferably include bisphenol A type polycarbonate resins (for example, Iupilon E series of Mitsubishi Gas Chemical Company, Inc.) and bisphenol Z type polycarbonate resins (for example, Iupilon Z series of Mitsubishi Gas Chemical Company, Inc.) represented by the following structural formulae; copolymer polycarbonates which have bisphenol A or bisphenol Z, and biphenol carbonate as structural units and which are disclosed in Japanese Patent Application Publication No. Hei 4-179961; and the like.

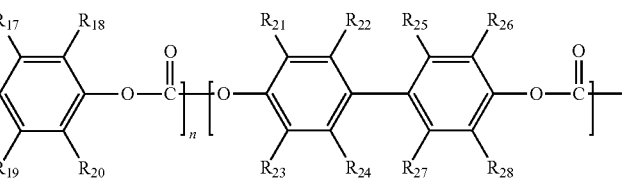

Polycarbonate (F)

Bisphenol A type carbonate (G)

Bisphenol Z type carbonate (H)

Specific examples of the biphenol copolymer carbonates include a bisphenol A/biphenol type polycarbonate resin represented by the following structural formula (I) (where it is preferable that n/n+m=0.1 to 0.9), and a more specific example is one represented by the formula (J) where n/n+m=0.85.

Bisphenol/biphenyl type copolymer polycarbonate (I)

Bisphenol A/biphenyl type copolymer polycarbonate (J)
(n/n + m = 0.85)

(where $R_{11}$ and $R_{12}$ each independently represent a hydrogen atom, an alkyl group, or an aryl group; $R_{11}$ and $R_{12}$ may be bonded to each other to form a ring; $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, and $R_{28}$ each independently represent a hydrogen atom, a halogen atom, an alkyl group, or an aryl group; and n and m represent the numbers of moles of the above-described repeating units, respectively.)

Moreover, besides the above-described polycarbonates, a polycarbonate (K) can be used which is disclosed in Japanese Patent Application Publication No. Hei 6-214412 and whose repeating unit is represented by the following structural formula.

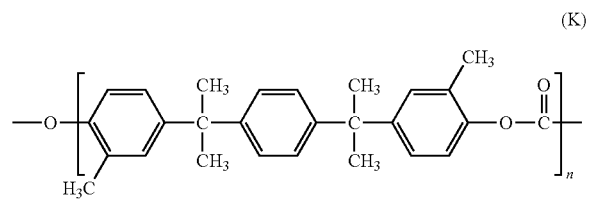

(K)

Moreover, a polycarbonate disclosed in Japanese Patent Application Publication No. Hei 6-222581 can also be used. The polycarbonate has a repeating unit represented by the following structural formula (L).

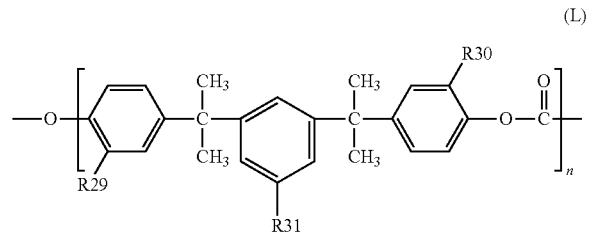

(L)

(where $R_{29}$, $R_{30}$, and $R_{31}$ may be the same or different, and each represent a hydrogen atom, a halogen atom, an alkyl group, a cycloalkyl group, an aryl group, or an arylalkyl group.)

Moreover, it is also possible to preferably use polymer binders which are shown in Japanese Patent Application Publication No. Hei 5-88398 and Japanese Patent Application Publication No. Hei 11-65136 and into which a siloxane unit represented by the following general formula (M) or (N) is introduced.

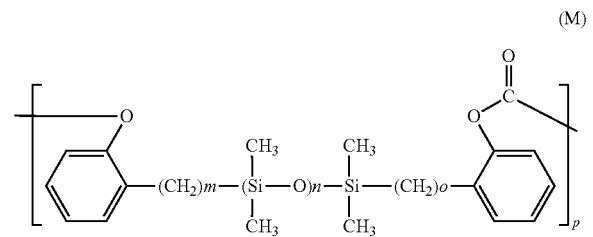

(M)

(where m, n, o, and p are each an integer representing the number of the corresponding repeating units.)

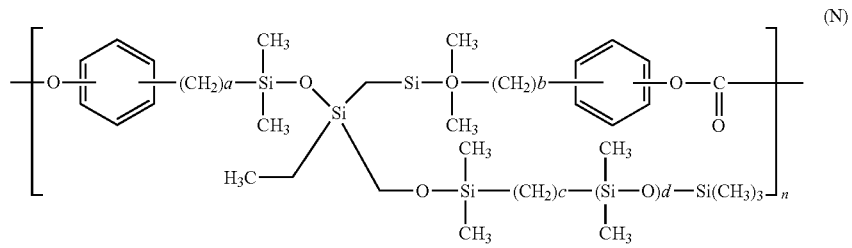

(N)

(where a, b, c, d, and n are each an integer representing the number of the corresponding repeating units.)

Regarding the blending ratio of each of these binder polymers with Compound (1), the charge transport material can be added in an amount of 10 to 1000 parts by weight, preferably 30 to 500 parts by weight, more preferably 40 to 200 parts by weight per 100 parts by weight of the binder polymer.

The solvent used is not particularly limited, and an organic solvent can be used. It is possible to use one of or a mixture of alcohols such as methanol, ethanol, and isopropanol; ketones such as acetone, methyl ethyl ketone, and cyclohexanone; amides such as N,N-dimethylformamide and N,N-dimethylacetamide; sulfoxides such as dimethyl sulfoxide; ethers such as tetrahydrofuran, dioxane, and ethylene glycol dimethyl ether; esters such as ethyl acetate and methyl acetate; aliphatic halogenated hydrocarbons such as methylene chloride, chloroform, 1,2-dichloroethane, dichloroethylene, carbon tetrachloride, and trichloroethylene; aromatic compounds such as benzene, toluene, xylene, chlorobenzene, and dichlorobenzene; and the like.

As the conductive substrate used for the photoreceptor of the present invention, a foil or a plate of a metal or an alloy of copper, aluminum, silver, iron, zinc, nickel, or the like is used. The foil or plate is shaped into a sheet or a drum before use. Alternatively, a conductive substrate obtained by vacuum-depositing or electrolytically plating such a metal onto a plastic film, cylinder, or the like, or a conductive substrate obtained by providing a layer of a conductive compound such as a conductive polymer, indium oxide, or tin oxide onto a substrate such as a glass substrate, a paper substrate or a plastic film by application or vapor deposition.

The application can be conducted by a coating method such as a dip coating method, a spray coating method, a spinner coating method, a wire-bar coating method, a blade coating method, a roller coating method, or a curtain coating method. For drying, it is preferable to conduct heat drying after drying at room temperature. The heat drying is preferably conducted at a temperature of 30 to 200° C. for 5 minutes to 2 hours in a windless state or under air stream.

Moreover, the electrophotographic photoreceptor of the present invention may contain charge transport agents other than the tris(4-styrylphenyl)amine derivative, and also may contain various additives, if needed. Examples of these other charge transport agents include, but are not limited to, hydrazone compounds represented by the following general formula (O) described in Japanese Examined Patent Application Publication No. Sho 55-42380, Japanese Patent Application Publication No. Sho 60-340999, Japanese Patent Application Publication No. Sho 61-23154, and the like; triphenylamine dimers represented by the following general formula (P) described in Japanese Examined Patent Application Publication No. Sho 58-32372 and the like; distyryl compounds represented by the following general formula (Q) described in U.S. Pat. No. 3,873,312 and the like; tetraphenylbutadiene-based compounds; triphenylmethane; and the like.

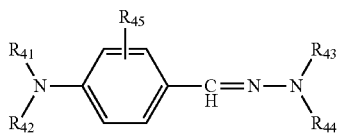

(where $R_{41}$ and $R_{42}$ may be the same or different, and each represent a lower alkyl group, an aryl group which may have one or more substituents, or an aralkyl group which may have one or more substituents; $R_{43}$ and $R_{44}$ may be the same or different, and each represent a lower alkyl group which may have one or more substituents, an aryl group which may have one or more substituents, an aralkyl group which may have one or more substituents, a heterocyclic group which may have one or more substituents; $R_{43}$ and $R_{44}$ may be bonded to each other to form a ring; $R_{45}$ represents a hydrogen atom, a lower alkyl group, an aryl group which may have one or more substituents, an aralkyl group which may have one or more substituents, a lower alkoxy group, or a halogen atom; and $R_{45}$ may be bonded to $R_{41}$ or $R_{42}$ to form a ring.)

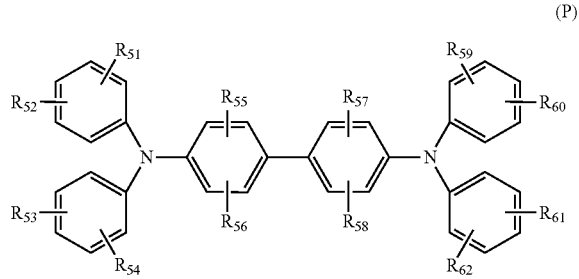

(where $R_{51}$ to $R_{62}$ may be the same or different, and each represent a hydrogen atom, a lower alkyl group, a lower alkoxy group, a halogen-atom-substituted lower alkoxy group, an aryl group which may have one or more substituents, or a halogen atom.)

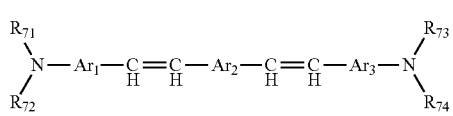

(where $R_{71}$ to $R_{74}$ may be the same or different, and each represents a lower alkyl group, or an aryl group which may have one or more substituents; and $Ar_1$, $Ar_2$, and $Ar_3$ may be the same or different, and each represent a phenylene group which may have one or more groups selected from lower alkyl groups, lower alkoxy groups, aryloxy groups, and halogen atoms.)

Examples of the various additives include plasticizers such as biphenylene-based compounds (for example, those disclosed in Japanese Patent Application Publication No. Hei 6-332206), m-terphenyl, and dibutyl phthalate; surface lubricants such as silicone oil, graft type silicone polymers, and various fluorocarbons; potential stabilizers such as dicyanovinyl compounds and carbazole derivatives; monophenol-based antioxidants such as 2,6-di-tert-butyl-4-methylphenol; bisphenol-based antioxidants; diamine-based antioxidants described in Japanese Patent Application Publication No. Sho 56-117244 or Japanese Patent Application Publication No. 2009-20204; amine-based antioxidants such as 4-diazabicyclo[2,2,2]octane; salicylic acid-based antioxidants; tocopherols; and the like.

When the electrophotographic photoreceptor of the present invention is a multilayer type electrophotographic photoreceptor, the film thickness of the charge transport layer is preferably 5 to 40 μm, and more preferably 10 to 30 μm. The charge transport layer obtained as described above is electrically connected to a charge generation layer, and has functions of receiving carriers injected through the charge generation layer in the presence of the electric field, and transporting these carriers across the charge transport layer to a surface opposite to the surface in contact with the charge generation layer. In this case, the charge transport layer may be stacked above or below the charge generation layer, and the charge transport layer is preferably staked above the charge generation layer. If needed, a protective layer can be provided on the thus prepared photoreceptor layer. In addition, an underlayer having a barrier function and an adhesive function can also be provided between the conductive substrate and the photoreceptor layer. Examples of materials for forming the underlayer include polyvinyl alcohol, nitrocellulose, casein, ethylene-acrylic acid copolymers, polyamides such as nylon, polyurethane, gelatin, aluminum oxide, and the like. The film thickness of the underlayer is preferably 0.1 to 5 μm, and more preferably 0.5 to 3 μm.

The charge generation layer can be prepared as a vapor deposition layer or an coating layer by using one material or a combination of materials selected from inorganic charge generation agents such as selenium, selenium-tellurium, and amorphous silicon; cationic dyes such as pyrylium salt-based dyes, thiapyrylium-based dyes, azulenium salt-based dyes, thiacyanine-based dyes, and quinocyanine-based dyes; polycyclic quinone pigments such as squarylium salt-based pigments, phthalocyanine-based pigments, anthanthrone-based pigments, dibenzpyrenequinone-based pigments, and pyranthrone pigments; organic charge generation agents such as indigo-based pigments, quinacridone-based pigments, azo pigments, and pyrrolopyrrole-based pigments. Of the above-described organic charge generation agents, organic charge generation agents described in Chem. Rev., 1993, 93, p. 449-486 are particularly preferable. Specifically, phthalocyanine-based pigments are preferable.

Examples of the phthalocyanine-based pigments include alkoxytitanium phthalocyanine (Ti(OR)$_2$Pc), oxotitanium phthalocyanine (TiOPc), copper phthalocyanine (CuPc), metal-free phthalocyanine (H$_2$Pc), chlorogallium phthalocyanine (ClGaPc), hydroxygallium phthalocyanine (HOGaPc), vanadyl phthalocyanine (VOPc), and chloroindium phthalocyanine (ClInPc). More specific examples of TiOPc include α-TiOPc, β-TiOPc, γ-TiOPc, m-TiOPc, Y-TiOPc, A-TiOPc, B-TiOPc, and amorphous TiOPc. Of these kinds of TiOPc, particularly preferable are one having the most intense peak at a Bragg angle (2θ±2°) of 27.2°, or one having main peaks at Bragg angles (2θ±2°) of 7.6° and 28.6°, in an X-ray diffraction spectrum obtained by using CuKα as the radiation source. Examples of H$_2$Pc include α-H$_2$Pc, β-H$_2$Pc, τ-H$_2$Pc, and x-H$_2$Pc.

Azo pigments are also preferable as the charge generation agent, and examples thereof include monoazo compounds, bisazo compounds, and trisazo compounds. Specifically, azo compounds represented by the following structural formulae are preferable.
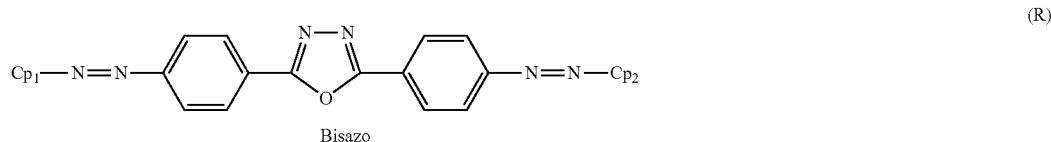
Bisazo
(R)
Cp1, Cp2;
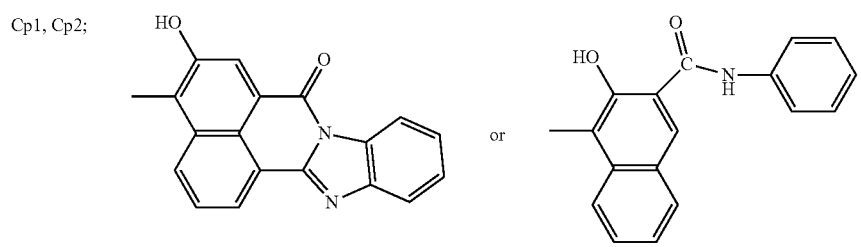
or
(S)
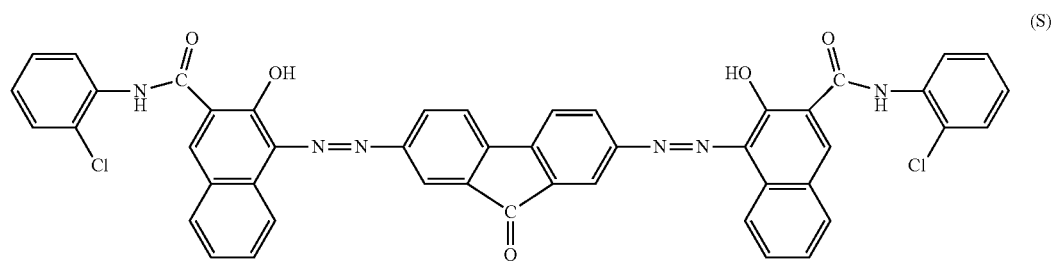
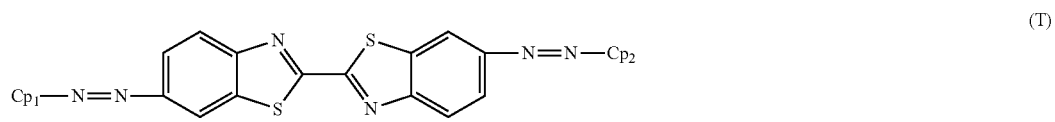
(T)
Cp1, Cp2;
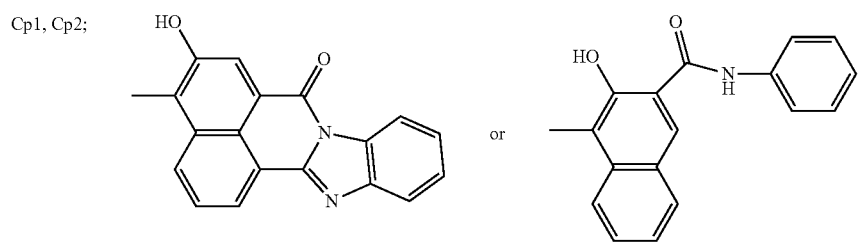
or
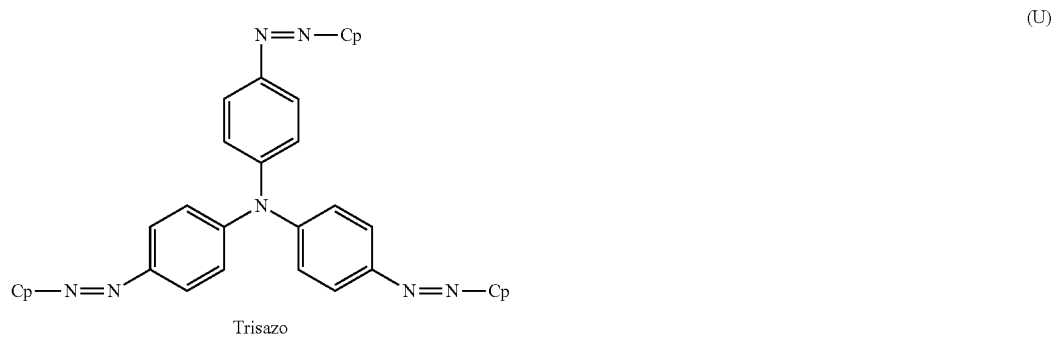
Trisazo
(U)

Cp;

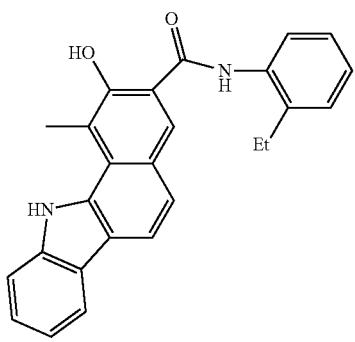

Moreover, a perylene-based compound represented by the following structural formula (V) or a polycyclic quinone-based compound represented by the structural formula (W) is preferable as the charge generation agent.

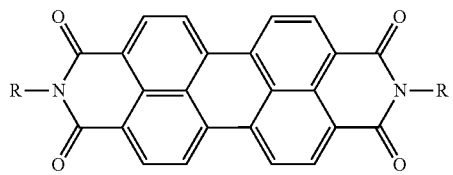

(where R represents a hydrogen atom, lower alkyl group, or aryl group which may have a substituent.)

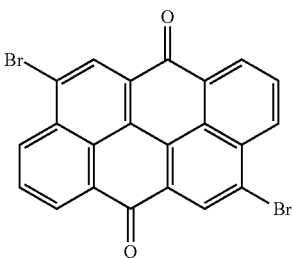

Any charge generation agent other than those charge generation agents can be used, as long as the charge generation agent is a material which generates charges at a high efficiency upon absorption of light.

As described above, the electrophotographic photoreceptor containing the tris(4-styrylphenyl)amine derivative of the present invention can be obtained.

EXAMPLES

The present invention will be described in detail below with reference to the following non-limiting Examples and Comparative examples. Note that measuring apparatuses and measurement conditions employed in Synthesis Examples were as follows:
(1) 1H-NMR apparatus: DRX-500 apparatus (500 MHz) manufactured by Bruker Corporation, internal standard substance: tetramethylsilane
Measured in deuterated chloroform or deuterated dimethyl sulfoxide
(2) MASS spectrometer: Hitachi M-80B (manufactured by Hitachi, Ltd.)
(3) HPLC apparatus: GL7400 Series (manufactured by GL Sciences Inc.)
ODS-3 (4.6×250 mm), dichloromethane:acetonitrile=5:95, 1 ml/min. Measured at UV 254 nm Synthesis Example 1

Synthesis of Compound (1-1)

To 29.0 g (207 mmol) of α-chloro-m-xylene, 37.8 g (228 mmol) of triethyl phosphite was added. The mixture was heated under reflux for 10 hours to obtain 52.3 g of a colorless liquid. Then, 47.3 g (187 mmol) of the colorless liquid was dissolved in 300 ml of N,N,-dimethylformamide (DMF), and 27.6 g (197 mmol) of p-chlorobenzaldehyde was added thereto. Under a nitrogen atmosphere, 23.1 g (206 mmol) of potassium-tert-butoxide was added thereto, followed by an additional stirring for 2 hours. The resulting mixture was neutralized with water and hydrochloric acid, and extracted with toluene. The toluene layer was washed with water, then concentrated, and subjected to a recrystallization operation. As a result, 36.6 g of a stilbene derivative was obtained. The yield was 85.6%.

Under a nitrogen atmosphere, 34.5 g (150 mmol) of the obtained stilbene derivative, 13.5 g (141 mmol) of sodium tert-butoxide, 1.1 g (47 mmol) of lithium amide, 172 mg (0.47 mmol) of [PdCl(allyl)]$_2$, and 441 mg (1.13 mmol) of 1,1-diphenyl-2-(dicyclohexylphosphino)propene were added into 160 ml of xylene, and the mixture was heated to 100° C. After stirring for 5 hours, water was added thereto, and further toluene was added thereto. Then, the organic layer was separated. The organic layer was washed with water, and then concentrated. The residue was subjected to silica gel column chromatography to remove impurities, and further subjected to a recrystallization operation. As a result, 24.0 g of a yellow crystal was obtained. The yield was 86%. An HPLC analysis showed that the ratio of the ttt isomer was 100%. Moreover, 1H NMR showed that the cis-trans ratio of the double bonds was 0:100.

1H NMR (CDCl$_3$): δ; 2.38 (s, 9H), 7.00 (d, J=16.3 Hz, 3H), 7.07 (d, J=7.4 Hz, 3H), 7.07 (d, J=16.3 Hz, 3H), 7.11 (d, J=8.6 Hz, 6H), 7.24 (t, J=7.5 Hz, 3H), 7.31 (d, J=8.1 Hz, 3H), 7.33 (s, 3H), 7.42 (d, J=8.6 Hz, 6H).

MS (m/Z) 593 mp 98-99° C.

Synthesis Example 2

Synthesis of Compound (1-2)

To 54.8 g (340 mmol) of p-chlorobenzyl chloride, 54.9 g (330 mmol) of triethyl phosphite was added, and the mixture was heated under reflux for 6 hours, followed by prification by distillation. As a result, 81.5 g of a colorless liquid was obtained. The yield was 94.0%. Into 300 ml of N,N,-dimethylformamide (DMF), 56.3 g (215 mmol) of the colorless liquid was dissolved, and further 30.7 g (226 mmol) of m-anisaldehyde was added thereto. Under a nitrogen atmosphere, 26.5 g (237 mmol) of potassium-tert-butoxide was added thereto, and the mixture was further stirred for 2 hours. The resultant mixture was neutralized with water and hydrochloric acid, and extracted with toluene. The toluene layer was washed with water, then concentrated, and subjected to a recrystallization operation. As a result, 43.2 g of a stilbene derivative was obtained. The yield was 82.3%.

Under a nitrogen atmosphere, 41.5 g (170 mmol) of the obtained stilbene derivative, 15.3 g (159 mmol) of sodium tert-butoxide, 1.2 g (53 mmol) of lithium amide, 194 mg (0.53 mmol) of [PdCl(allyl)]$_2$, and 496 mg (1.27 mmol) of 1,1-diphenyl-2-(dicyclohexylphosphino)propene were added into 150 ml of xylene, and the mixture was heated to 100° C. After stirring for 5 hours, water was added thereto, and further toluene was added thereto. Then, the organic layer was separated. The organic layer was washed with water, and then concentrated. The residue was subjected to silica gel column chromatography to remove impurities, and further subjected to a recrystallization operation. As a result, 30.0 g of a yellow crystal was obtained. The yield was 88%. An HPLC analysis showed that the ratio of the ttt isomer was 100%. Moreover, 1H NMR showed that the cis-trans ratio of the double bonds was 0:100.

1H NMR (CDCl$_3$): δ; 3.86 (s, 9H), 6.80-6.82 (m, 3H), 7.00 (d, J=16.2 Hz, 3H), 7.04 (t, J=2.0 Hz, 3H), 7.07 (d, J=16.3 Hz, 3H), 7.10-7.12 (m, 9H), 7.27 (t, J=7.9 Hz, 3H), 7.41-7.43 (m, 6H).

MS (m/Z) 641 mp 145-146° C.

Comparative Synthesis Example 1

Synthesis of Comparative Compound (1)

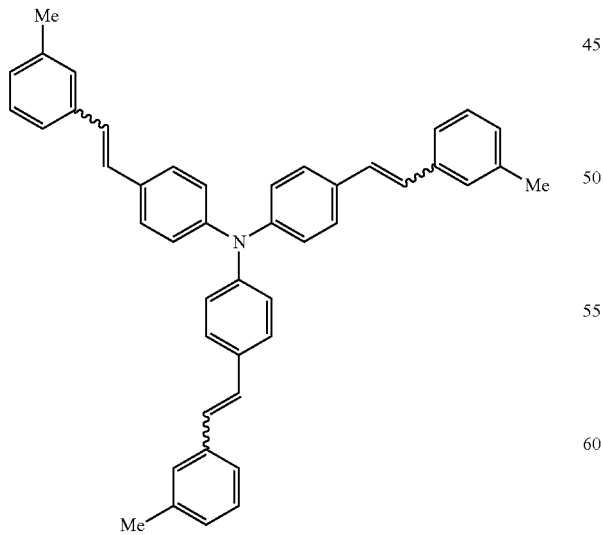

Comparative Compound (1)
(ttt isomer ratio: 12%)

Comparative Compound (1) was synthesized in the same manner as in Synthesis Example 1, except that a cis-trans mixture (cis:trans=52:48 (calculated based on 1H NMR)) was used instead of the stilbene derivative (5). The yield was 70%. An HPLC analysis showed that the ratio of the ttt isomer was 12%. Moreover, 1H NMR showed that the cis-trans ratio of the double bonds was 51:49.

1H NMR (DMSO-d$_6$): δ; 2.25 (m, 9H), 6.51-6.58 (m, cis, 6H), 6.84-7.56 (m, trans, 6H, Ar—H 24H)

MS (m/Z) 593

Comparative Synthesis Example 2

Synthesis of Comparative Compound (2)

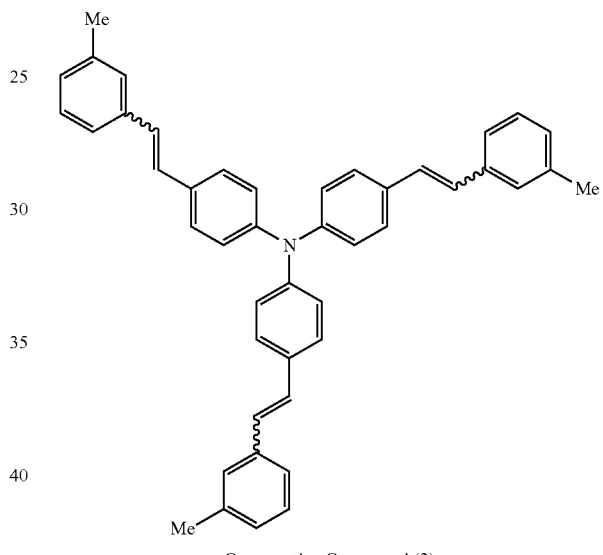

Comparative Compound (2)
(ttt isomer ratio: 1%)

Comparative Compound (2) was synthesized in the same manner as in Synthesis Example 1, except that a cis-trans mixture (cis:trans=82:18 (calculated based on 1H NMR)) was used instead of the stilbene derivative (5). The yield was 72%. An HPLC analysis showed that the ratio of the ttt isomer was 1%. Moreover, 1H NMR showed that the cis-trans ratio of the double bonds was 78:22.

1H NMR (DMSO-d$_6$): δ; 2.25 (m, 9H), 6.51-6.58 (m, cis, 6H), 6.84-7.56 (m, trans, 6H, Ar—H 24H)

MS (m/Z) 593

Comparative Synthesis Example 3

Synthesis of Comparative Compound (3)

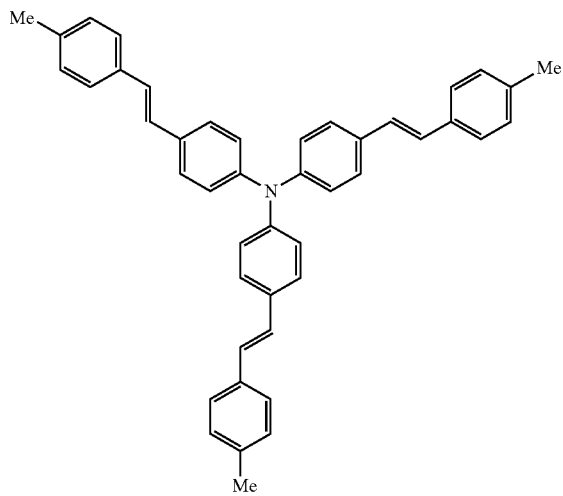

Comparative Compound (3)
(ttt isomer ratio: 100%)

Comparative Compound (3) was synthesized in the same manner as in Synthesis Example 2, except that p-tolualdehyde was used instead of m-anisaldehyde. The yield was 76%. An HPLC analysis showed that the ratio of the ttt isomer was 100%. Moreover, 1H NMR showed that the cis-trans ratio of the double bonds was 0:100.

1H NMR (CDCl$_3$): δ; 2.36 (s, 9H), 6.99 (d, J=16.3 Hz, 3H), 7.03 (d, J=16.2 Hz, 3H), 7.09-7.11 (m, 6H), 7.16 (d, J=7.9 Hz, 6H), 7.39-7.41 (m, 12H)

MS (m/Z) 593

Comparative Synthesis Example 4

Synthesis of Comparative Compound (4)

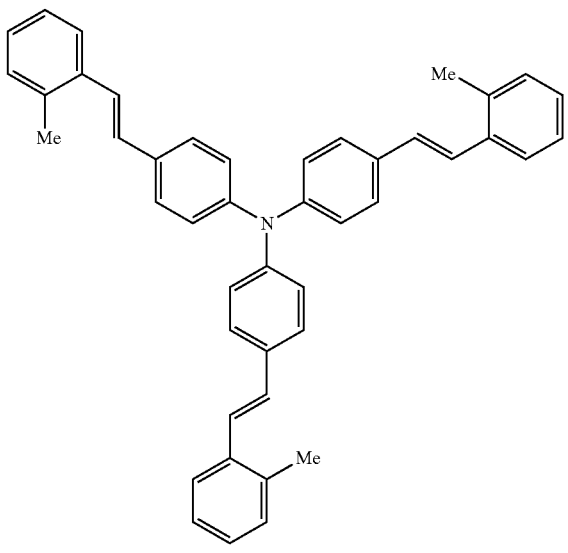

Comparative Compound (4)
(ttt isomer ratio: 100%)

Comparative Compound (4) was synthesized in the same manner as in Synthesis Example 1, except that α-chloro-o-xylene was used instead of α-chloro-m-xylene. The yield was 85%. An HPLC analysis showed that the ratio of the ttt isomer was 100%. Moreover, 1H NMR showed that the cis-trans ratio of the double bonds was 0:100.

1H NMR (CDCl$_3$): δ; 2.43 (s, 9H), 6.97 (d, J=16.1 Hz, 3H), 7.12-7.14 (m, 6H), 7.17-7.22 (m, 9H), 7.25 (d, J=16.2 Hz, 3H), 7.43-7.45 (m, 6H), 7.59 (d, J=7.5 Hz, 3H)

MS (m/Z) 593

Comparative Synthesis Example 5

Synthesis of Comparative Compound (5)

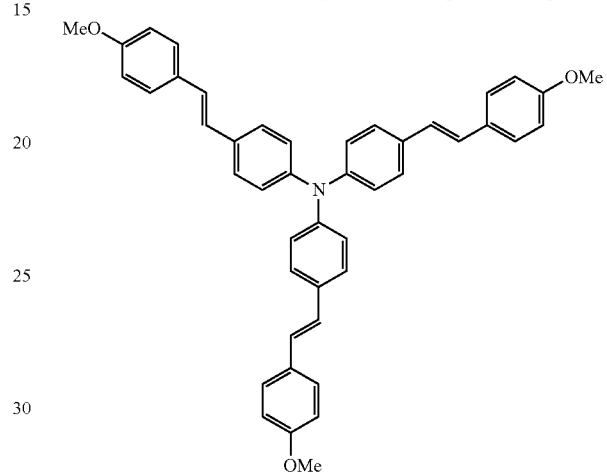

Comparative Compound (5)
(ttt isomer ratio: 100%)

Comparative Compound (5) was synthesized in the same manner as in Synthesis Example 2, except that p-anisaldehyde was used instead of m-anisaldehyde. The yield was 60%. An HPLC analysis showed that the ratio of the ttt isomer was 100%. Moreover, 1H NMR showed that the cis-trans ratio of the double bonds was 0:100.

1H NMR (CDCl$_3$): 3.83 (s, 9H), 6.89-6.93 (m, 9H), 7.03 (d, J=16.3 Hz, 3H), 7.29-7.31 (m, 6H), 7.40-7.42 (m, 6H), 7.43-7.45 (m, 6H)

MS (m/Z) 641

Example 1

Into 85 parts by weight of tetrahydrofuran, 15 parts by weight of "Panlite TS-2020" (manufactured by Teijin Chemicals Ltd.) and 15 parts by weight of Compound (1-1) were dissolved by mixing. The solution was applied by using a doctor blade onto a sheet in which aluminum was vapor deposited on a polyethylene phthalate (PET) film, followed by drying at 80° C. for 3 hours. Thus, a charge transport layer was formed (thickness: 18 μm). Further, a translucent gold electrode was vapor deposited on this charge transport layer, and the charge carrier mobility was measured. For the measurement of the carrier mobility, a nitrogen gas laser having a pulse half width of 0.9 sec and a wavelength of 337 nm was used as a light source, and the time-of-flight method (Toshiaki Tanaka, Yasuhiro Yamaguchi and Masaaki Yokoyama, Denshi Shashin (Electrophotography), 29, 366 (1990)) was employed. Table 1 and FIG. 1 show the results measured at 25° C. and 25 V/μm.

Examples 2 and 3

In Examples 2 and 3, Compound (1-1) and Comparative Compound (2) were blended to provide the ratios of the ttt isomer determined by HPLC analysis of 70% and 50%, respectively. The mobilities of these mixture samples were measured in the same manner as in Example 1. Table 1 and FIG. 1 show the results.

Comparative Examples 1 to 3

In Comparative Examples 1 to 3, Compound (1-1) and Comparative Compound (2) were blended to provide the ratios of the ttt isomer determined by HPLC analysis of 40%, 30% and 20%, respectively. The mobilities of these mixture samples were measured in the same manner as in Example 1. Table 1 and FIG. 1 show the results.

Comparative Examples 4 to 9

Experiments were conducted by using Comparative Compounds (1) to (6) in the same manner as in Example 1. Table 1 shows the results. Note that it was impossible to measure the mobility of Comparative Compounds (3) to (5) because of their insolubility.

Comparative Compound 6

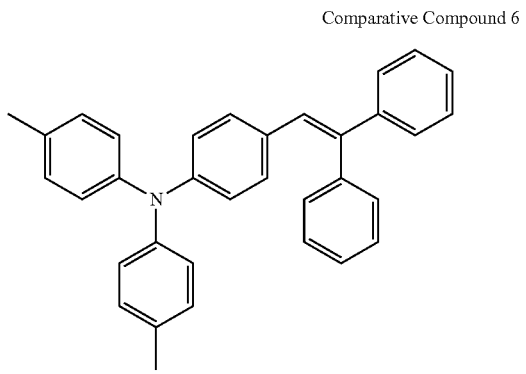 [SMILES: Cc1ccc(N(c2ccc(C)cc2)c2ccc(C=C(c3ccccc3)c3ccccc3)cc2)cc1]

TABLE 1

| | | ttt isomer (%) (calculated on the basis of HPLC) | Hole mobility $\mu$ (cm$^2$/Vs) |
|---|---|---|---|
| Example 1 | Exemplified Compound (1-1) | 100 | $4.2 \times 10^{-5}$ |
| Example 2 | mixture sample of Exemplified Compound (1-1) and Comparative Compound (2) | 70 | $4.2 \times 10^{-5}$ |
| Example 3 | mixture sample of Exemplified Compound (1-1) and Comparative Compound (2) | 50 | $4.1 \times 10^{-5}$ |
| Comparative Example 1 | mixture sample of Exemplified Compound (1-1) and Comparative Compound (2) | 40 | $3.5 \times 10^{-5}$ |
| Comparative Example 2 | mixture sample of Exemplified Compound (1-1) and Comparative Compound (2) | 30 | $3.1 \times 10^{-5}$ |
| Comparative Example 3 | mixture sample of Exemplified Compound (1-1) and Comparative Compound (2) | 20 | $1.7 \times 10^{-5}$ |
| Comparative Example 4 | Comparative Compound (1) | 12 | $1.5 \times 10^{-5}$ |
| Comparative Example 5 | Comparative Compound (2) | 1 | $1.1 \times 10^{-5}$ |
| Comparative Example 6 | Comparative Compound (3) | 100 | impossible to measure because of insolubility |
| Comparative Example 7 | Comparative Compound (4) | 100 | impossible to measure because of insolubility |
| Comparative Example 8 | Comparative Compound (5) | 100 | impossible to measure because of insolubility |
| Comparative Example 9 | Comparative Compound (6) | — | $2.0 \times 10^{-5}$ |

As is apparent from Table 1, it can be seen that Compound (1-1) exhibited a higher mobility than Comparative Compounds 1 and 2, which had lower ratios of the ttt isomer. Moreover, it can be seen that Compound (1-1) exhibited a greater mobility than Comparative Compound (6), which is generally known as a high mobility material. Meanwhile, Comparative Compounds 3, 4, and 5, which had likewise high ratios of the ttt isomers, were not successfully dissolved in the binder polymer solutions, and no films were formed successfully therefrom. In other words, it can be understood that the position of the substituent is important in the cases of tris(4-styrylphenyl)amine derivatives.

Moreover, it can be understood from FIG. 1 that, when the ratio of the ttt isomer is 50% or higher, the high mobility characteristics are not impaired, and a higher mobility than that of Comparative Compound (6) can be obtained.

Examples 4 and 5

Into 2500 parts by weight of methanol, 37.5 parts by weight of "FINE RESIN 104" (manufactured by Namariichi Co., Ltd.) was dissolved. The solution was applied onto a sheet in which aluminum was vapor deposited on a polyethylene phthalate (PET) film, followed by drying at 105° C. for 1 hour. Thus, an underlayer was obtained.

An coating liquid was obtained by dissolving 22.5 parts by weight of metal-free phthalocyanine "Fastgen Blue 8120BS" (manufactured by DIC Corporation) and, as a binder, 15 parts by weight of a butyral resin "S-LEC BH-3" (manufactured by Sekisui Chemical Co., Ltd.) into 750 parts by weight of methyl ethyl ketone and 750 parts by weight of cyclohexanone. The coating liquid was applied onto the underlayer, followed by drying at 80° C. for 2 hours. Thus, a charge generation layer was formed.

Into 8 parts by weight of tetrahydrofuran, 1 part by weight of a polycarbonate "Z-200" (manufactured by Mitsubishi Engineering-Plastics Corporation) and 1 part by weight of Compound (1-1) or (1-2) were dissolved by mixing. The liquid was applied onto the charge generation layer, followed by drying at 80° C. for 2 hours, to thereby form a charge transport layer (thickness: approximately 20 μm). Thus, each electrophotographic photoreceptor was prepared.

The characteristics of the electrophotographic photoreceptors thus obtained were measured in a static method using an electrostatic paper analyzer "EPA-8300A" (manufactured by Kawaguchi Electric Works). Specifically, each electrophotographic photoreceptor was charged by a corona discharge of −6 kV, and the surface potential $V_0$ (Unit: −V) was measured. The electrophotographic photoreceptor was kept in the dark for 5 seconds (the surface potential Vi (Unit: −V)), and then irradiated with a laser light of 0.2 μW and 780 nm. Thereafter, the exposure necessary for decaying the surface potential Vi by half, namely, the half decay exposure $E_{1/2}$ (μJ/cm$^2$) was determined, and the surface residual potential Vr (Unit: −V) after irradiation for 5 seconds was determined. Table 2 shows the results.

Comparative Examples 10 to 14

Experiments were conducted by using Comparative Compounds (2) to (6) in the same manner as in Example 4. Table 2 shows the results. Note that it was impossible to measure the electrophotographic characteristics of Comparative Compounds (3) to (5) because of their insolubility.

TABLE 2

| | | $V_0$ (−V) | $V_i$ (−V) | $V_r$ (−V) | $E_{1/2}$ (μJ/cm$^2$) | Remarks |
|---|---|---|---|---|---|---|
| Example 4 | Compound (1-1) | 447 | 439 | 104 | 0.071 | |
| Example 5 | Compound (1-2) | 421 | 411 | 101 | 0.072 | |
| Comparative Example 10 | Comparative Compound (2) | 496 | 488 | 143 | 0.077 | |
| Comparative Example 11 | Comparative Compound (3) | — | — | — | — | impossible to measure because of insolubility |
| Comparative Example 12 | Comparative Compound (4) | — | — | — | — | impossible to measure because of insolubility |
| Comparative Example 13 | Comparative Compound (5) | — | — | — | — | impossible to measure because of insolubility |
| Comparative Example 14 | Comparative Compound (6) | 485 | 478 | 134 | 0.074 | |

As is apparent from Table 2, it can be seen that the electrophotographic photoreceptors using Compound (1-1) and (1-2) were more sensitive (had smaller $E_{1/2}$ values) and had smaller residual potentials (Vr) than the electrophotographic photoreceptors using Comparative Compounds (2) and (6). Meanwhile, Comparative Compounds (3), (4), and (5), which had likewise high ratios of the ttt isomers, were not successfully dissolved in the binder polymer solutions, and no films were formed successfully therefrom. In other words, it can be understood that the position of the substituent is important in the cases of tris(4-styrylphenyl)amine derivatives.

Examples 6 and 7

Into 85 parts by weight of tetrahydrofuran, 15 parts by weight of "Panlite TS-2020" and 15 parts by weight of Compound (1-1) or (1-2) were dissolved by mixing. This liquid was applied onto a PET plate by using a doctor blade, followed by drying at 80° C. for 3 hours. Thus, a thin film was prepared (thickness: approximately 20 μm).

The obtained thin film was subjected to an abrasion test using "Suga Abrasion Tester NUS-ISO3" (manufactured by Suga Test Instruments Co., Ltd.). Specifically, the thin film was ground with "precision finishing abrasive film #4000" (manufactured by Sumitomo 3M Limited) 400 times, 800 times, or 1200 times, and the weight losses of the thin film were measured. Table 3 shows the results.

Comparative Examples 15 to 17

Experiments were conducted by using Comparative Compounds (3) to (5) in the same manner as in Example 6. Table 3 shows the results. Note that it was impossible to perform measurement of Comparative Compounds (3) to (5) because of their insolubility.

Comparative Example 18

An experiment was conducted in the same manner as in Example 6, except that Comparative Compound (7) represented by the following formula was used. Table 3 shows the results.

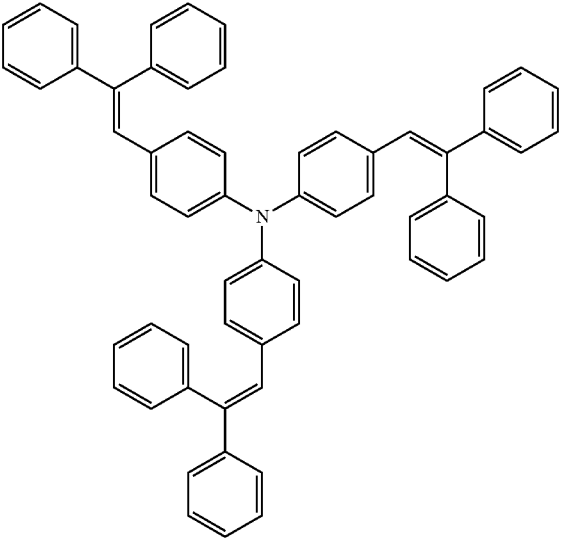

Comparative Compound 7

TABLE 3

| | | Weight loss after abrasion (mg) | | | |
|---|---|---|---|---|---|
| | | 400 times | 800 times | 1200 times | |
| Example 6 | Compound (1-1) | 0.9 | 1.4 | 2.4 | |
| Example 7 | Compound (1-2) | 1.1 | 1.9 | 2.8 | |
| Comparative Example 15 | Comparative Compound (3) | — | — | — | impossible to measure because of insolubility |
| Comparative Example 16 | Comparative Compound (4) | — | — | — | impossible to measure because of insolubility |
| Comparative Example 17 | Comparative Compound (5) | — | — | — | impossible to measure because of insolubility |
| Comparative Example 18 | Comparative Compound (7) | 1.4 | 2.8 | 4.1 | |

As is apparent from the Table 3, the thin films using the Compound (1-1) and (1-2) underwent less weight losses, and had better abrasion resistances. These results indicate that these thin films had better film stabilities.

Examples 8 and 9

Each of the Exemplified Compounds (1-1) and (1-2) was dissolved in 1 g of tetrahydrofuran at 25° C. Table 4 shows the weight of the compound dissolved completely.

Comparative Examples 19 to 21

Experiments were conducted by using Comparative Compounds (3) to (5) in the same manner as in Example 8. Table 4 shows the results.

TABLE 4

| | | Solubility (g/g tetrahydrofuran) (25° C.) |
|---|---|---|
| Example 8 | Compound (1-1) | 0.40 |
| Example 9 | Compound (1-2) | 0.45 |
| Comparative Example 19 | Comparative Compound (3) | 0.08 |
| Comparative Example 20 | Comparative Compound (4) | 0.02 |
| Comparative Example 21 | Comparative Compound (5) | 0.10 |

As is apparent from Table 4, the compounds (1-1) and (1-2) had better solubilities. This allows formation of higher-concentration organic thin films from the compounds (1-1) and (1-2).

The invention claimed is:

1. A tris(4-styrylphenyl)amine derivative represented by the following general formula (2):

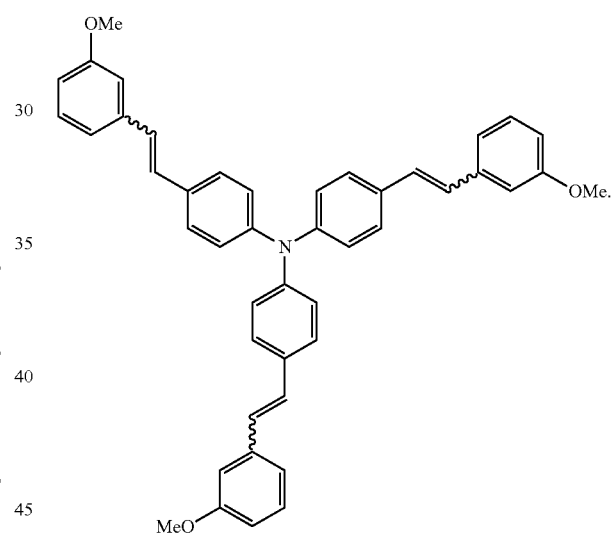

(2)

* * * * *